United States Patent [19]
Miskewitz

[11] Patent Number: 5,702,687
[45] Date of Patent: Dec. 30, 1997

[54] CHEWING GUM PRODUCT WITH PLAQUE-INHIBITING BENEFITS

[75] Inventor: Regina M. Miskewitz, Somerville, N.J.

[73] Assignee: Church & Dwight Co., Inc., Princeton, N.J.

[21] Appl. No.: 539,010

[22] Filed: Oct. 3, 1995

[51] Int. Cl.⁶ .............. A61K 9/68; A61K 7/16; A61K 7/18; A61K 33/10
[52] U.S. Cl. .............. 424/52; 424/48; 424/49; 424/440; 424/458; 424/489; 424/717
[58] Field of Search .............. 424/48, 43, 54, 424/40, 52, 458, 489, 717

[56] References Cited

U.S. PATENT DOCUMENTS

| | | | |
|---|---|---|---|
| 4,269,860 | 5/1981 | Ogawa et al. | 426/5 |
| 4,639,368 | 1/1987 | Niazi et al. | 424/48 |
| 4,749,575 | 6/1988 | Rotman | 424/441 |
| 4,800,087 | 1/1989 | Mehta | 424/497 |
| 4,837,008 | 6/1989 | Rudy et al. | 424/53 |
| 4,952,407 | 8/1990 | Record et al. | 426/3 |
| 4,971,782 | 11/1990 | Rudy et al. | 424/53 |
| 4,978,528 | 12/1990 | Degre | 514/2 |
| 5,077,051 | 12/1991 | Gallopo et al. | 424/435 |
| 5,084,278 | 1/1992 | Mehta et al. | 424/441 |
| 5,098,725 | 3/1992 | Rotman et al. | 426/98 |
| 5,380,530 | 1/1995 | Hill | 424/48 |
| 5,411,750 | 5/1995 | Lajoie et al. | 424/717 |
| 5,417,963 | 5/1995 | Murphy et al. | 514/965 |
| 5,424,077 | 6/1995 | Lajoie | 514/951 |
| 5,433,960 | 7/1995 | Meyers | 426/5 |
| 5,466,470 | 11/1995 | Lajoie | 424/641 |
| 5,482,701 | 1/1996 | Winston | 424/65 |
| 5,482,702 | 1/1996 | Murphy et al. | 424/65 |
| 5,518,727 | 5/1996 | Lajoie et al. | 424/400 |

*Primary Examiner*—Shep K. Rose
*Attorney, Agent, or Firm*—Irving Fishman

[57] ABSTRACT

The present invention provides a chewing gum product which has a content of two or more active ingredients for improved dental health. In one embodiment a present invention chewing gum product has a content of ingredients which include a gum base, dispersed particles of organic-encapsulated sodium bicarbonate, a bulking sweetener, a plaque-inhibiting ingredient, and a flavorant.

8 Claims, No Drawings

CHEWING GUM PRODUCT WITH PLAQUE-INHIBITING BENEFITS

CROSS-REFERENCE TO RELATED APPLICATION

The subject matter of the present patent application is related to that disclosed in copending patent application Ser. No. 08/538,215, filed Oct. 3, 1995; incorporated by reference.

BACKGROUND OF THE INVENTION

Dental research has developed substantial evidence that dental plaque is the predominant etiological factor responsible for both periodontal disease and dental caries. Dental caries is the localized, progressive decay of the teeth. It results from tooth demineralization brought about by acids formed when bacteria in dental plaque ferment carbohydrate foods present in the mouth.

Dental plaque is a deposit which accumulates on the teeth and adjacent surfaces in the oral cavity. The plaque is a product of microbial growth, primarily derived from food residues in the mouth. Mucoproteins and minerals present from the saliva and dead cells in the mouth also assist in plaque formation.

Plaque is removed to some extent by effective brushing of the teeth, but the less accessible and more sheltered areas of the mouth which cannot be readily reached by a toothbrush, are particularly susceptible to plaque and eventual calculus growth. Left unhindered, the plaque increases in size and more tenaciously adheres to the teeth. The bacterial metabolism within the plaque on the tooth surface results in the production of acids, toxins and enzymes which are deleterious to the neighboring oral tissues. There is evidence pointing to plaque as being the direct cause of dental caries, due to the generation of acids within the plaque structure.

To protect a normal tooth, a thin layer of dental enamel forms a protective coating over the tooth. This coating consists mainly of calcium, phosphate, and other ions in a hydroxyapatite-like structure. The enamel contains 2–5 percent carbonate, which makes the enamel susceptible to acid dissolution.

The interaction of three factors is believed to result in dental caries: a susceptible tooth surface; microflora; and suitable substrate for the microflora. Although several acidogenic microorganisms that are present in the mouth can initiate carious lesions, Streptococcus mutans is believed to be the primary pathogen.

It is known that foods containing fermentable carbohydrates can promote dental caries. Tooth decay begins when the Streptococcus mutans, that reside principally in the plaque that adheres to a tooth surface, metabolize the fermentable carbohydrates consumed by the host. During the metabolism of the fermentable carbohydrates by the bacteria, lactic acid and other organic acids are secreted as a by-product. These acids reduce the pH of the surrounding plaque/tooth environment.

When the pH of the plaque/tooth environment drops below a critical level of 5.5 to 5.7, hydroxyapatite (calcium phosphate hydroxide, $Ca_{10}(PO_4)_6(OH)_2$), the key component of tooth enamel, begins to dissolve. Typically, the dissolution begins below the tooth's porous surface.

With repeated acid attacks, caused by the further metabolism of fermentable carbohydrates by the bacteria, subsurface lesions expand. If the lesions expand to the point that the enamel surface breaks, a cavity is formed and the process is no longer reversible.

The natural remineralization process involves, in part, the flow of saliva over the plaque. The saliva can raise the pH of the environment. Additionally, calcium and phosphate ions in the saliva precipitate out to replace the hydroxyapatite that was dissolved by the organic acids created during the metabolism of the fermentable carbohydrates.

Typically, this remineralization process only occurs at significant levels when the pH is above the critical level. If the saliva does not sufficiently raise the pH, significant remineralization will not occur. The remineralization process may be enhanced by fluoride in the oral cavity that speeds up new crystal growth and makes a fluorapatite-like material that is precipitated on the surface of the crystals inside the carie lesion.

The most important single factor contributing to periodontal disease is the accumulation of plaque and dental calculus (e.g., salivary tartar) on the teeth. These deposits result in tissue inflammation of the surrounding gingiva, and, as the condition increases in severity, the supporting bone is also affected. These reactions lead to the destruction of the supporting structures and the subsequent mass loss of teeth which are usually free of decay.

Although brushing the teeth with a toothbrush and dentifrice is a widely recognized technique for maintaining dental health, the average American brushes only about once a day for approximately one minute. Therefore, a great need exists for finding additional methods for improving daily oral hygiene. Chewing gum has over the years been advocated as a possible excellent adjunct for cleaning the teeth, because people find chewing of gum very pleasurable and chew gum for much longer periods of time than they brush their teeth. Chewing gum is especially advantageous for use in circumstances where toothbrushing is not possible or convenient, such as after lunch, while traveling, or while working.

In general, chewing gum comprises a neutral and tasteless masticatory chewing gum base and one or more non-masticatory active ingredients mixed into the base. As used herein, an "active ingredient" is an ingredient such as a sweetener; a flavoring agent which determines flavor and taste characteristics of the gum; a body-treating ingredient such as a medicinal drug or pharmaceutical agent which is released at a gradual rate and ingested during chewing; or a breath-freshening ingredient which treats or reduces oral malodor. In addition, the chewing gum may contain water-soluble and usually sweet non-masticatory bulking agents, a coloring agent, or a plasticizing agent which is employed to improve the texture of the gum.

Certain active chewing gum ingredients benefit from or require encapsulation in order to achieve a gradual and controlled release of the ingredients during chewing or to promote their stability in chewing gum.

U.S. Pat. No. 5,139,794 describes a chewing gum which has a content of an encapsulated sodium chloride ingredient. The coating on the sodium chloride particles provides a prolonged flavor-enhancing effect without imparting a salty taste.

Of background interest with respect to the present invention are publications which disclose chewing gum products containing a bicarbonate salt such as sodium bicarbonate. Prior art references include U.S. Pat. Nos. 4,148,872; 4,150, 112, 4,156,715; 4,156,716; 4,157,385; 4,159,315; 4,160, 054; 4,160,820; 4,170,633; 4,269,860; 4,639,368; 4,867, 989; 4,952,407; 4,997,667; 5,077,051; and the like.

There is continuing interest in the development of novel chewing gum products which provide dental health benefits during normal usage.

Accordingly, it is an object of this invention to provide a chewing gum product which can serve as a convenient adjunct for improved dental health.

It is another object of this invention to provide a chewing gum product which has a content of encapsulated therapeutic ingredient for oral hygiene which is sustain-released over a prolonged period under oral chewing conditions.

It is a further object of this invention to provide a chewing gum product which counteracts bacteria-generated acids, enhances saliva flow, and exhibits plaque-inhibiting activity.

Other objects and advantages of the present invention shall become apparent from the accompanying description and examples.

DESCRIPTION OF THE INVENTION

One or more objects of the present invention are accomplished by the provision of a chewing gum product comprising between about 15–80 weight percent of a gum base, and between about 1–30 weight percent of dispersed particles of an organic-encapsulated alkali metal bicarbonate ingredient.

In another embodiment this invention provides a chewing gum product comprising (1) between about 15–80 weight percent of a gum base; (2) between about 1–30 weight percent of dispersed particles of an organic-encapsulated alkali metal bicarbonate ingredient; (3) between about 0–25 weight percent of alkali metal bicarbonate powder ingredient; (4) between about 0.01–8 weight percent of a plaque-inhibiting ingredient; (5) between about 5–70 weight percent of a water-soluble bulking ingredient; (6) between about 0–5 weight percent of a flavorant ingredient; (7) between about 0–0.2 weight percent of a colorant ingredient; (8) between about 0–20 weight percent of an abrasive ingredient; (9) between about 0–3 weight percent of a surfactant ingredient; (10) between about 0–3 weight percent of a fluoridating ingredient; and (11) between about 0–15 weight percent of glycerin or lecithin or a mixture thereof.

A present invention chewing gum may be any variety of different chewing gum types including low and high moisture, sugar or sugarless, wax-containing or wax-free, low calorie, and the like, and can contain other health agents.

A chewing gum product generally consists of a water-insoluble gum base, a water-soluble portion, and flavors. The water-soluble portion dissipates over a period of time, and the gum base portion is retained during mastication.

A conventional chewing gum base usually contains an elastomer, an elastomer solvent, and various other ingredients such as fillers, softeners, plasticizers and emulsifiers. Gum base raw materials are described in U.S. Pat. Nos. 2,366,589; 3,821,417; 3,984,574; 4,041,179; 4,170,633; 4,400,372; 4,590,075; and 5,378,131; incorporated by reference. The history and development of chewing gum products is elaborated in "Chewing Gum" by A. H. Suck, (Haarmann & Reimer, Second Edition), incorporated by reference.

Chewing gum base elastomers for stick gum and dragees include chicle, jelutong, balata, crown gum, guttapercha, sorva, butadiene-styrene copolymer, polyisobutylene, isobutylene-isoprene copolymer, polyethylene, and the like, and mixtures thereof.

Chewing gum base elastomer solvents include pentaerythritol ester of wood rosin, glycerol ester of polymerized rosin, partially hydrogenated methyl ester of rosin, and the like.

Chewing gum base waxes include natural wax, polyethylene wax, paraffin wax, beeswax, carnauba wax, microcrystalline wax, and the like.

Chewing gum base compositions for stick gum and dragees are commercially available under tradenames such as Paloja T, Firm Paloja T and Nova T (L. A. Dreyfus Corp.). Bubble gum bases are available as Paloja Bubble T, Ladco Bubble T and Grande Bubble T (L. A. Dreyfus Corp).

An essential ingredient of a present invention chewing gum composition is between about 1–30 weight percent of a dispersed particle phase of an organic-encapsulated alkali metal bicarbonate ingredient.

The alkali metal bicarbonate core matrix of the encapsulated particles is sodium bicarbonate or potassium bicarbonate or a mixture thereof. Optionally, the alkali metal bicarbonate core matrix of the encapsulated particles can have a content between about 0.1–20 weight percent of alkali metal carbonate, based on the weight of alkali metal bicarbonate core matrix content. The alkali metal carbonate can be a sodium or potassium salt or a mixture thereof.

The average particle size of the encapsulated alkali metal bicarbonate ingredient can range between about 20–200 microns. The organic encapsulant of the coated particles typically comprises between about 5–60 weight percent of the encapsulated alkali metal bicarbonate particles.

The organic encapsulant of the coated particles is selected from hydrophilic and hydrophobic (water-insoluble) film-forming agents, and mixtures thereof, such as hydrocolloids and polysaccharides.

The term "hydrophilic" as employed herein refers to an encapsulant film-forming agent which has a water-solubility of at least about two grams per one hundred grams of water at 25° C.

The organic encapsulant can consist of 100% hydrophilic encapsulant, or 100% water-insoluble encapsulant, or any mixture thereof. The rate of alkali metal bicarbonate release during mastication of a chewing gum product is directly related to the hydrophilicity of the encapsulant coating on the alkali metal bicarbonate particles. A hydrophilic encapsulant coating will sustain-release the core alkali metal bicarbonate content over a period of about 20 minutes. A water-insoluble encapsulant coating will sustain-release the alkali metal bicarbonate over a period of about 35 minutes. An organic encapsulant can comprise a hydrophilic polymer having a content between about 5–80 weight percent of a water-insoluble polymer.

Suitable hydrophilic encapsulants for coating the alkali metal bicarbonate particles include gum arabic, gum karaya, gum tragacanth, guar gum, locust bean gum, xanthan gum, carrageenan, alginate salt, casein, dextran, pectin, agar, sorbitol, 2-hydroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene oxide, polyvinyl alcohol/acetate, and the like. Polyvinyl acetate is illustrative of a water-insoluble polymer which can be included as an additional coating component to moderate the hydrophilicity of a hydrophilic polymer coating.

Suitable water-insoluble encapsulants include polyvinyl acetate, polyacrylamide, polyvinyl chloride, polystyrene, polyethylene, polyurethane, polymethacrylate, paraffin wax, carnauba wax, beeswax, stearyl alcohol, zein, shellac, edible fat, and the like. Encapsulants utilized in chewing gum products are disclosed in U.S. Pat. Nos. 4,673,577, 5,139, 794 and 4,933,190, incorporated by reference.

The encapsulant can be applied to the alkali metal bicarbonate particles by conventional coating means, such as rotating disk, fluidized bed, spray drying, freeze drying, tumbling, coacervation, and the like.

In another embodiment a present invention chewing gum product has a content between about 0.5–25 weight percent of particulate alkali metal bicarbonate ingredient which is not encapsulated. The unencapsulated alkali metal bicarbonate can contain between about 0.1–20 weight percent of alkali metal carbonate, based on the weight of unencapsulated alkali metal bicarbonate.

The unencapsulated alkali metal bicarbonate ingredient typically can have an average particle size between about 10–250 microns. In a preferred embodiment, the alkali metal bicarbonate is in micronized form, and has an average particle size between about 0.5–20 microns.

During mastication of a chewing gum product containing both encapsulated and unencapsulated alkali metal bicarbonate ingredients, the product provides both immediate and long lasting oral hygiene benefits. There is a clean taste and breath refreshment, and a prolonged deodorizing effect on mouth odor.

In another essential aspect, between about 0.01–8 weight percent of a plaque-inhibiting ingredient is incorporated in a present invention chewing gum product. Suitable plaque-inhibiting agents include zinc compounds and polyphosphate compounds.

Illustrative of zinc compounds with plaque-inhibiting properties are zinc oxide, zinc silicate, zinc carbonate, zinc phosphate, zinc stannate, zinc tetrafluoroborate, zinc hexafluorosilicate, zinc citrate, zinc benzoate, zinc oxalate, zinc stearate, zinc chloride, zinc sulfate, zinc nitrate, zinc phenolsulfonate, zinc carboxymethylsuccinate, and the like. The zinc compound also can be in the form of a complex, with a complexing reagent such as polyethylenimine or ethylenediamine tetraacetic acid.

Illustrative of polyphosphate compounds with plaque-inhibiting properties are dialkali metal and tetraalkali metal pyrophosphate and mixtures thereof in a hydrated or unhydrated form. Illustrative of pyrophosphate salts are $Na_2H_2P_2O_7$, $Na_4P_2O_7$ and $K_4P_2O_7$. Other suitable polyphosphates include hydrated or unhydrated alkali metal tripolyphosphates such as $Na_5P_3O_{10}$ and $K_5P_3O_{10}$.

In another embodiment a present invention chewing gum product has a content between about 5–70 weight percent of a water-soluble bulking ingredient.

The term "water-soluble" as employed herein refers to a chewing gum ingredient which has a solubility of at least about five grams per one hundred grams of water at 25° C.

The water-soluble bulking ingredient in a chewing gum product typically includes bulk sweeteners, high-potency sweeteners, flavorants, softeners, emulsifiers, colorants, fillers, antioxidants, and other constituents which contribute desirable attributes.

Between about 0.1–15 weight percent of a softener ingredient can be added to enhance the chewability and mouth feel of the chewing gum. The softener ingredient can comprise glycerin or lecithin or a mixture thereof, which additionally functions as a humectant.

The bulking ingredient can comprise between about 5–70 weight percent of a bulking sweetener. Bulking sweeteners can consist of sugar and/or sugarless constituents. Sugar sweeteners are illustrated by saccharides such as sucrose, glucose, maltose, dextrin, dried invert sugar, fructose, levulose, galactose, corn syrup solids, and the like.

Sugarless sweeteners are illustrated by polyhydric alcohols such as sorbitol, mannitol, xylitol, hydrogenated starch hydrolysates, maltitol, and the like.

Between about 0.025–2 weight percent of a high intensity sweetener ingredient can be utilized alone or in combination with a bulk sweetener. High intensity sweeteners are illustrated by aspartame, saccharin, cyclamate, thaumatin, dihydrochalcones, acesulfame K compounds, and the like. Long lasting sweeteners can be achieved by encapsulating a portion or all of a high intensity sweetener ingredient. A higher content of high intensity sweetener can be employed when it is encapsulated. Encapsulants and coating techniques can be used which are similar to those described herein for an encapsulated alkali metal bicarbonate ingredient.

Between about 0.02–5 weight percent of a flavorant ingredient is usually incorporated in a present invention chewing gum product. Suitable flavorants include menthol, peppermint oil, spearmint oil, wintergreen oil, cinnamon oil, anise, and the like. The flavorant can be encapsulated, as described in U.S. Pat. Nos. 3,826,847; 5,128,155; and 5,266,335, incorporated by reference.

A present invention chewing gum product optionally can contain between about 0.001–0.2 weight percent of a colorant ingredient, such as FD&C-type dyes and lakes. The colorant can be in the form of particles which give the gum matrix a speckled appearance. The speckled effect also can be incorporated in a surface coating, such as the coating on dragee gum products. Speckled gum products are described in U.S. Pat. No. 4,744,991, incorporated by reference.

A chewing gum product additionally can contain between about 0.01–3 weight percent of an antioxidant ingredient such as butylated hydroxytoluene, butylated hydroxyanisole, propyl gallate, and the like.

Between about 1–20 weight percent of an abrasive ingredient also can be included in a present invention chewing gum product to provide a dentifrice cleaning action, in addition to the abrasive activity of the alkali metal bicarbonate ingredient. Suitable abrasives include a powder form of phosphate and silica compounds such as calcium phosphate, silica xerogel, and the like. Other types of suitable abrasives are described in U.S. Pat. Nos. 4,170,633 and 4,891,211, incorporated by reference.

The compatibility of the ingredients in a chewing gum product, and the enhancement of flavor, can be accomplished by the inclusion of between about 0.001–3 weight percent of a surfactant ingredient in the chewing gum product.

Suitable anionic surfactants include alkali metal and ammonium $C_8$–$C_{30}$ aliphatic-containing carboxylate, sulfonate, sulfate and phosphate salts, such as sodium dioctyl sulfosuccinate, sodium lauryl sulfate, sodium dodecylbenzenesulfonate, ammonium lignosulfonate, and the like.

Suitable nonionic surfactants include condensation products of alkylene oxide with fatty alcohols, amines and alkylphenols, such as ethoxylated sorbitan monostearate, ethoxylated glycerol monostearate, and the like.

Suitable cationic surfactants include cetyltrimethylammonium bromide, cetylpyridinium chloride, benzyldimethylstearylammonium chloride, and the like. This type of surfactant additionally imparts antibacterial activity to a chewing gum product.

Other surfactants which are suitable for inclusion in a chewing gum product are described in U.S. Pat. No. 3,930,026, incorporated by reference.

A present invention chewing gum product also can contain between about 0.05–3 weight percent of a fluoridating ingredient for the prevention of dental caries. Fluoridating agents are illustrated by alkali metal fluoride, ammonium fluoride, stannous fluoride, stannous chlorofluoride, potassium stannous fluoride, alkali metal monofluorophosphate, ammonium monofluorophosphate, and the like.

A present invention chewing gum product can be produced in accordance with conventional manufacturing processes, such as those described in U.S. Pat. No. 4,329,369, and as demonstrated in the following examples.

A present invention chewing gum product provides a novel combination of properties which function as a convenient adjunct to other oral hygiene vehicles such as toothpastes and mouthwashes.

In a further embodiment this invention provides a method of oral hygiene which comprises orally masticating a present invention chewing gum product in accordance with a regimen which satisfies personal need and convenience.

The encapsulated alkali metal bicarbonate ingredient of a present invention chewing gum product is sustain-released over a prolonged period under gum mastication conditions.

A present invention chewing gum product provides dental cleaning action, and counteracts bacteria-generated acids, enhances saliva flow, and exhibits plaque-inhibiting and tartar-control activities.

The alkali metal bicarbonate ingredient of a present invention chewing gum product contributes oral care benefits such as dental cleaning and whitening, and a prolonged period of mouth odor reduction. Other derived advantages are perceptions of breath refreshment and a pleasant mouthfeel during gum chewing.

The following examples are further illustrative of the present invention. The components and specific ingredients are presented as being typical, and various modifications can be derived in view of the foregoing disclosure within the scope of the invention.

EXAMPLE I

This Example illustrates the particle size distribution of sodium bicarbonate before and after air-jet milling.

Commercial grade sodium bicarbonate (3DF, Church & Dwight) is processed by air-jet milling (Particle Size Technology, Inc.), and the particle size distribution of milled samples is determined in comparison with unmilled samples by means of a Microtrac laser-scattering particle size analyzer.

The 3DF sodium bicarbonate has an average particle size of 31.4 microns, and the micronized 3DF sodium bicarbonate has an average particle size of 9.8 microns.

The middle 80% of particle size distribution is between 15.4 and 55.8 microns for the 3DF sodium bicarbonate, and between 4.3 and 21.5 microns for the micronized form.

EXAMPLE II

This Example illustrates a fluidized bed procedure for encapsulating a particulate bicarbonate compound with an organic coating in accordance with the present invention.

A fluidized bed vessel is utilized which is equipped with a Wurster air-suspension coater system (WARF) as described in U.S. Pat. Nos. 4,568,559 and 4,877,621.

A coating solution is prepared by dissolving polyethylene glycol (45 g, Poly-G 2000, Olin Corp.), and propylene glycol butyl ether (10 g, PPG 14, Americol) in ethanol (500 g)/water (75 g).

Sodium bicarbonate is utilized as the core matrix crystallites. The sodium bicarbonate (Particle Size Technology, Inc.) has an average particle size and particle size distribution having correspondence with an Example I type of micronized powder.

The sodium bicarbonate powder is charged into the coating chamber of the coater system.

Compressed air is introduced into the coating chamber, and the organic coating solution is sprayed on the air-suspended bicarbonate core matrix crystallites, until the coating weight is about 30% of the total dry weight of the coated particles.

The procedure is repeated, except that hydroxypropylmethylcellulose (Methocel 60 HG, Dow Chemical Co.) is employed as the film-forming coating medium.

The procedure is repeated, except that maltodextrin (Lodex 10; Durkee Foods) or amylodextrin is employed as the coating medium, and 0.5 g of a surfactant is included in the solution (polyoxyethylenesorbitan monolaurate; Tween 20; ICI Americas, Inc.).

The coated particles consist of a continuous film coating on an inner core of between about 2–10 crystallites of sodium bicarbonate. The coated particles have an average particle size of about 40 microns.

The procedure is repeated except that a polyvinyl acetate (M.W. 40,000) is employed as the polymeric medium for coating the sodium bicarbonate particles.

EXAMPLE III

This Example illustrates the preparation of a chewing gum product in accordance with the present invention.

An invention chewing gum product is prepared by processing the following ingredients:

|  | Parts By Weight |
| --- | --- |
| Cafosa Luxor 225-01 gum base[1] | 23.92 |
| sorbitol liquid (70% solution) | 2.39 |
| sorbitol powder | 31.48 |
| mannitol powder | 14.35 |
| maltitol powder | 9.57 |
| sodium bicarbonate, micronized[2] | 4.78 |
| sodium bicarbonate, encapsulated[3] | 4.78 |
| peppermint oil | 1.44 |
| glycerin (96%) | 7.18 |
| sodium saccharin | 0.10 |
| zinc oxide, micronized[4] | 0.067 |
| Blue #2 Lake | 0.006 |

[1]Cafosa Co.
[2]Average particle size of 12 microns (Example I).
[3]Polyvinyl acetate coating (Example II).
[4]Average particle size of 3 microns.

The sorbitol, mannitol, maltitol, micronized sodium bicarbonate, encapsulated sodium bicarbonate powder, and zinc oxide are blended. About one third of the blend is added to the preheated gum base (122° F.) in a mixer unit, and the medium is mixed for about 3 minutes.

The liquid sorbitol and glycerin are combined to form a solution. About one half of the solution is added slowly to the mixer contents, and the medium is mixed for about 3 minutes.

The remaining dry blend and liquid solution portions are added with continuous mixing. The sodium saccharin and colorant are added with mixing, followed by the addition of the flavorant. The ingredient mass is mixed until homogeneous. The resultant chewing gum formulation is rolled, sheeted, sized and packaged as a stick chewing gum product.

EXAMPLE IV

This Example illustrates the preparation of a chewing gum product in accordance with the present invention.

An invention chewing gum product is prepared by processing the following ingredients:

|  | Parts By Weight |
|---|---|
| Cafosa Luxor 225-01 gum base[1] | 23.92 |
| sorbitol liquid (70% solution) | 2.39 |
| sorbitol powder | 31.48 |
| mannitol powder | 14.35 |
| maltitol powder | 9.57 |
| sodium bicarbonate, micronized[2] | 4.78 |
| sodium bicarbonate, encapsulated[3] | 4.78 |
| peppermint oil | 1.44 |
| glycerin (96%) | 7.18 |
| sodium saccharin | 0.10 |
| sodium tripolyphosphate powder | 3.17 |
| Blue #2 Lake | 0.006 |

[1]Cafosa Co.
[2]Average particle size of 12 microns (Example I).
[3]Polyvinyl acetate coating (Example II).

The sorbitol, mannitol, maltitol, micronized sodium bicarbonate, encapsulated sodium bicarbonate, sodium tripolyphosphate, and zinc oxide are blended. About one third of the blend is added to the preheated gum base (122° F.) in a mixer unit, and the medium is mixed for about 3 minutes.

The liquid sorbitol and glycerin are combined to form a solution. About one half of the solution is added slowly to the mixer contents, and the medium is mixed for about 3 minutes.

The remaining dry blend and liquid solution portions are added with continuous mixing. The sodium saccharin and colorant are added with mixing, followed by the addition of the flavorant. The ingredient mass is mixed until homogeneous. The resultant chewing gum formulation is rolled, sheeted, sized and packaged as a stick chewing gum product.

What is claimed is:

1. A chewing gum product comprising (1) between about 15-80 weight percent of a gum base; (2) between about 1-30 weight percent of dispersed particles of an organic-encapsulated alkali metal bicarbonate ingredient having an average particle size between about 20-200 microns; (3) between about 0.5-25 weight percent of alkali metal bicarbonate powder ingredient having an average particle size between about 0.5-20 microns; (4) between about 0.01-8 weight percent of a plaque-inhibiting ingredient; (5) between about 5-70 weight percent of a water-soluble bulking ingredient; (6) between about 0.2-5 weight percent of a flavorant ingredient; (7) between about 0-0.2 weight percent of a colorant ingredient; (8) between about 1-20 weight percent of an additional abrasive ingredient other than sodium bicarbonate; (9) between about 0-15 weight percent of a surfactant ingredient; (10) between about 0.05-3 weight percent of a fluoridating ingredient; and (11) between about 0-15 weight percent of glycerin or lecithin or a mixture thereof.

2. A chewing gum product in accordance with claim 1 wherein the plaque-inhibiting ingredient is a zinc compound.

3. A chewing gum product in accordance with claim 1 wherein the plaque-inhibiting ingredient is an alkali metal polyphosphate.

4. A chewing gum product in accordance with claim 1 wherein the bulking ingredient is a sweetener selected from the group consisting of sucrose, glucose, maltitol, xylitol, sorbitol and mannitol and mixtures thereof.

5. A chewing gum product in accordance with claim 1 which contains between about 0.001-0.2 weight percent of a colorant ingredient.

6. A chewing gum product in accordance with claim 1 which contains between about 0.001-3 weight percent of a surfactant ingredient.

7. A chewing gum product in accordance with claim 1 which contains between about 0.1-15 weight percent of glycerin or lecithin or a mixture thereof.

8. A method of oral hygiene which comprises orally masticating a claim 1 chewing gum product in accordance with a regimen which satisfies personal need and convenience.

* * * * *